United States Patent [19]
Merte et al.

[11] Patent Number: 5,464,388
[45] Date of Patent: Nov. 7, 1995

[54] CARDIOPLEGIA ADMINISTRATION SYSTEM AND METHOD

[75] Inventors: Kenneth E. Merte, Saline; William G. O'Neill, Ann Arbor, both of Mich.

[73] Assignee: Minnesota Mining and Manufacturing Company, St. Paul, Minn.

[21] Appl. No.: 383,940

[22] Filed: Feb. 6, 1995

Related U.S. Application Data

[62] Division of Ser. No. 154,925, Nov. 18, 1993, Pat. No. 5,423,749.

[51] Int. Cl.⁶ ................................................. A61M 39/00
[52] U.S. Cl. .......................... 604/153; 604/250; 604/247; 417/477.2; 222/144.5; 222/214
[58] Field of Search ............................... 604/80–86, 65, 604/246–247, 249–250, 258–259; 417/477; 222/144.5, 214, 325

[56] References Cited

U.S. PATENT DOCUMENTS

| | | |
|---|---|---|
| 3,776,249 | 12/1973 | Wailes et al. |
| 3,927,955 | 12/1975 | Spinosa et al. |
| 4,011,940 | 3/1977 | Neal et al. |
| 4,038,981 | 8/1977 | LeFevre et al. |
| 4,105,028 | 8/1978 | Sadlier et al. |
| 4,187,057 | 2/1980 | Xanthopoulos |
| 4,249,923 | 2/1981 | Walda |
| 4,256,437 | 3/1981 | Brown |
| 4,259,985 | 4/1981 | Bergmann |
| 4,333,486 | 6/1982 | Ciccozzi |
| 4,372,304 | 2/1983 | Avakian et al. |
| 4,425,113 | 1/1984 | Bilstad |
| 4,425,116 | 1/1984 | Bilstad et al. |
| 4,445,826 | 5/1984 | Tarr |
| 4,493,710 | 1/1985 | King et al. |
| 4,496,133 | 1/1985 | Sule |
| 4,512,764 | 4/1985 | Wunsch |
| 4,524,802 | 6/1985 | Lawrence et al. |

(List continued on next page.)

FOREIGN PATENT DOCUMENTS

| | | | |
|---|---|---|---|
| 0362822 | 4/1990 | European Pat. Off. | A61F 9/00 |
| 0529902 | 3/1993 | European Pat. Off. | A61M 1/00 |
| WO91/15149 | 10/1991 | WIPO | A61B 1/12 |
| WO93/19791 | 10/1993 | WIPO | A61M 1/00 |

OTHER PUBLICATIONS

Chapter 4 of a Master's Thesis entitled "A Digitally Controlled Experimental Apparatus for Cryogenic Preservation of the Rat Heart" by Kenneth E. Merte (1977).

Dodge et al. U.S. Ser. No. 08/003,475, filing date Jan. 12, 1993.

*Primary Examiner*—C. Fred Rosenbaum
*Assistant Examiner*—Perry E. Van Over
*Attorney, Agent, or Firm*—Gary L. Griswold; Walter N. Kirn; Stephen W. Bauer

[57] ABSTRACT

A cardioplegia administration system includes a tubing set, a positive displacement pump and a mixing system. The tubing set has a cardioplegia supply tube; a blood supply tube; and a cardioplegia administration tube connected to the cardioplegia and blood supply tubes. The positive displacement pump engages the cardioplegia administration tube to pump fluid therethrough. The mixing system includes pinch valves for alternately-continually pinching the cardioplegia and blood supply tubes to close and open the cardioplegia and blood supply tubes such that only one of the cardioplegia and blood supply tubes is open at a time, and a controller that controls the intervals during which the pinch valves are open to control the ratio of the cardioplegia medication and blood or blood substitute administered through the cardioplegia administration tube. The method of this invention includes the step, among others, of operating the pinch valves to close and open the cardioplegia and blood supply tubes so that only one of the cardioplegia and blood supply tubes is open at a time while controlling the intervals during which the pinch valves are open to control the ratio of the cardioplegia medication and blood or blood substitute administered through the cardioplegia administration tube.

18 Claims, 8 Drawing Sheets

U.S. PATENT DOCUMENTS

| | | |
|---|---|---|
| 4,526,515 | 7/1985 | DeVries. |
| 4,537,561 | 8/1985 | Xanthopoulos. |
| 4,559,036 | 12/1985 | Wunsch. |
| 4,626,241 | 12/1986 | Campbell et al.. |
| 4,637,813 | 1/1987 | DeVries. |
| 4,651,898 | 3/1987 | Bell. |
| 4,673,389 | 6/1987 | Archibald et al.. |
| 4,681,563 | 7/1987 | Deckert et al.. |
| 4,713,051 | 12/1987 | Steppe et al.. |
| 4,714,463 | 12/1987 | Archibald et al.. |
| 4,735,558 | 4/1988 | Kienholz et al.. |
| 4,793,589 | 12/1988 | Eldredge et al.. |
| 4,798,580 | 1/1989 | DeMeo et al.. |
| 4,830,581 | 5/1989 | Hendriks. |
| 4,842,584 | 6/1989 | Pastrone. |
| 4,846,177 | 7/1989 | Leonard. |
| 4,874,359 | 10/1989 | White et al.. |
| 4,887,636 | 12/1989 | Rothen. |
| 4,888,004 | 12/1989 | Williamson, IV et al.. |
| 4,889,148 | 12/1989 | Smazik. |
| 4,925,444 | 5/1990 | Orkin et al.. |
| 4,993,594 | 2/1991 | Becker et al.. |
| 4,998,914 | 3/1991 | Wiest et al.. |
| 5,044,902 | 9/1991 | Malbec. |
| 5,057,278 | 10/1991 | Maxwell et al.. |
| 5,094,260 | 3/1992 | Stuart et al.. |
| 5,094,820 | 3/1992 | Maxwell et al.. |
| 5,125,891 | 6/1992 | Hossain et al.. |
| 5,154,693 | 10/1992 | East et al.. |
| 5,181,842 | 1/1993 | Sunderland et al.. |
| 5,195,960 | 3/1993 | Hossain et al.. |
| 5,199,604 | 4/1993 | Palmer et al.. |
| 5,207,642 | 5/1993 | Orkin et al.. |
| 5,267,956 | 12/1993 | Beuchat. |
| 5,304,126 | 4/1994 | Epstein et al.. |
| 5,306,242 | 4/1994 | Joyce et al.. |
| 5,318,515 | 6/1994 | Wilk. |
| 5,320,502 | 6/1994 | Davis. |
| 5,328,057 | 7/1994 | Hellenberg et al.. |
| 5,350,083 | 9/1994 | Du. |
| 5,358,481 | 10/1994 | Todd et al.. |
| 5,385,540 | 1/1995 | Abbott et al.. |
| 5,403,277 | 4/1995 | Dodge et al.. |
| 5,403,281 | 4/1995 | O'Neill et al.. |

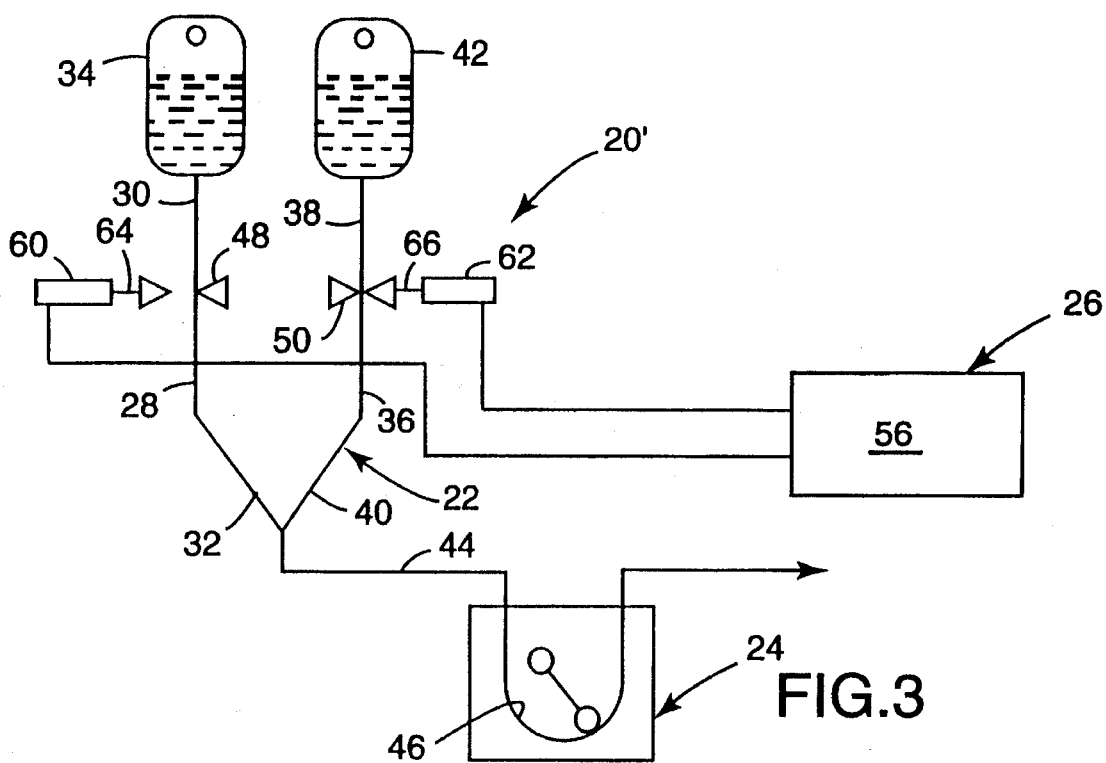
FIG.3
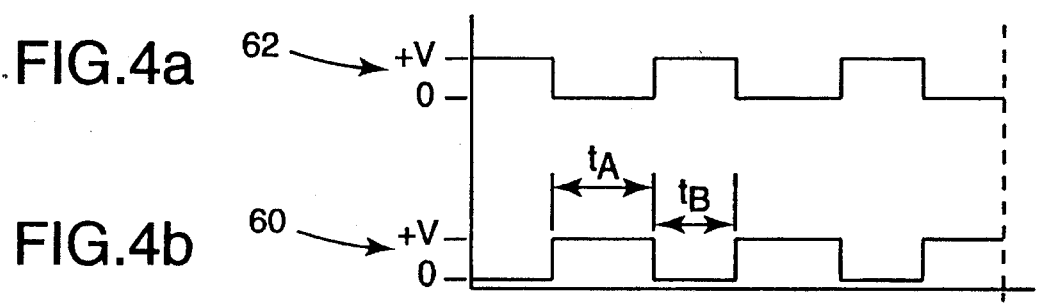

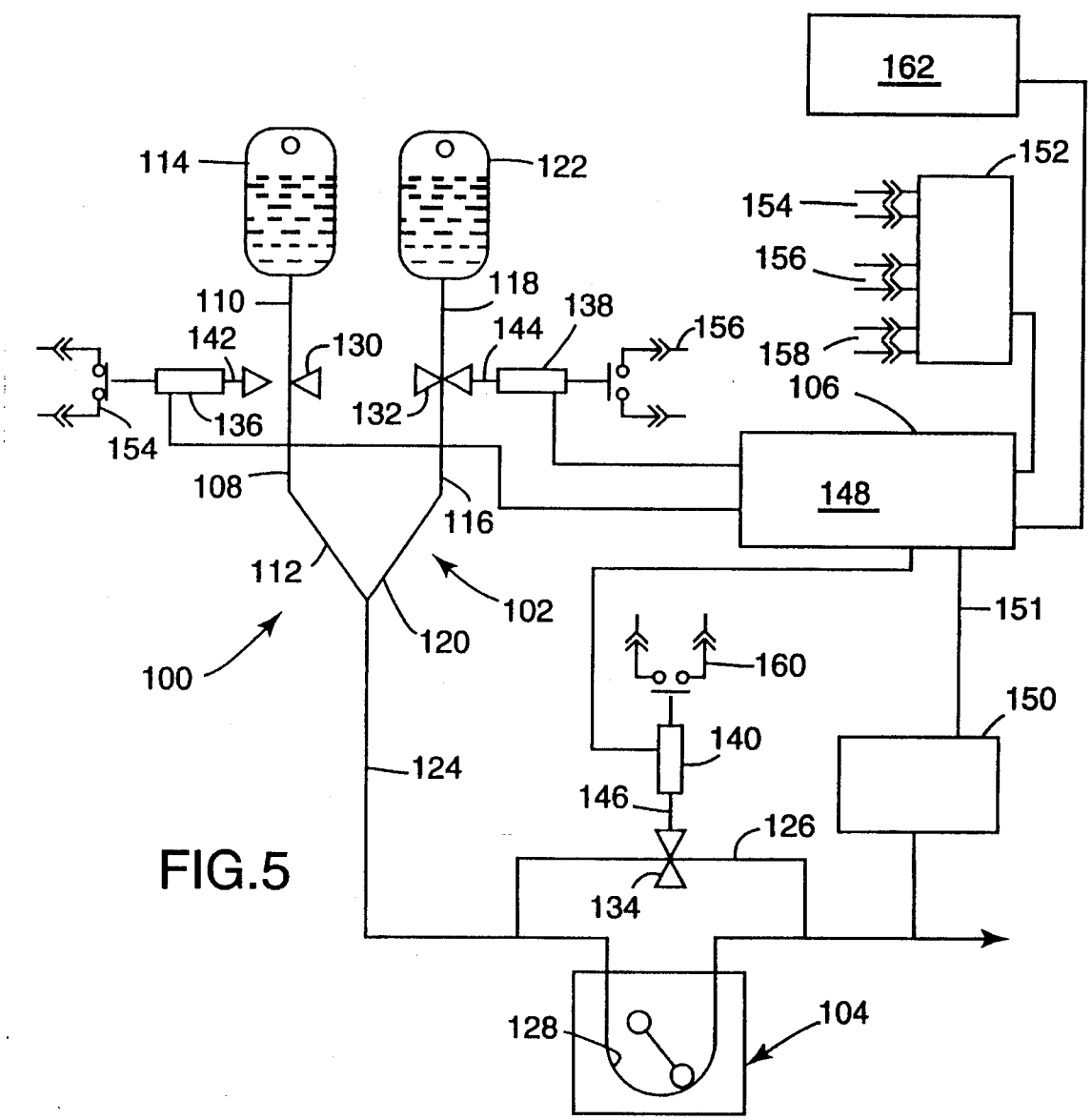
FIG.5
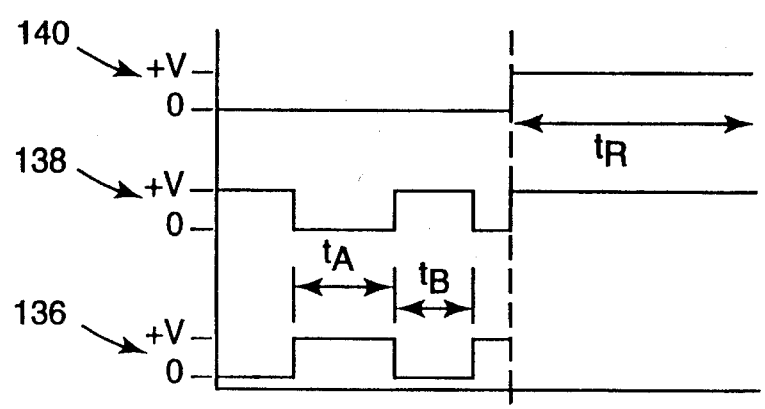
FIG.6a
FIG.6b
FIG.6c

CARDIOPLEGIA ADMINISTRATION SYSTEM AND METHOD

This application is a divisional application of application Ser. No. 08/154,925, filed Nov. 18, 1993, now U.S. Pat. No. 5,423,749.

This invention relates to an administration system for cardioplegia, and to a method of administering cardioplegia.

BACKGROUND AND SUMMARY OF THE INVENTION

Cardioplegia is a commonly used technique for protecting a heart during open heart surgery in which cardioplegia solution is circulated through the heart tissues. The cardioplegia solution typically comprises a mixture of a medication, such as a potassium solution, and blood or a blood substitute. The cardioplegia solution stops the heart and provides oxygen to minimize damage to the heart. The selection of the particular content of the cardioplegia solution depends upon the particular physician. Moreover, it is becoming common to vary the content of the cardioplegia solution during the procedure.

Until this invention, the adjustable mixing of the components of a cardioplegia solution has been accomplished by providing separate pumps for each component. However, providing multiple pumps is expensive. Using multiple pumps also makes it difficult to make adjustments in the composition of the cardioplegia solution without changing the flow rate, or to change the flow rate without changing the composition of the solution.

The cardioplegia system of the present invention is adapted for mixing and administering cardioplegia medication and/or blood to a patient's heart during cardiopulmonary bypass surgery. The system comprises a tubing set, a positive displacement pump, and a mixing system. The tubing set includes a cardioplegia supply tube adopted for connection to a source of cardioplegia medication; a blood supply tube adopted for connection to a source of blood or blood substitute; and a cardioplegia administration tube connected to the cardioplegia and blood supply tubes, the cardioplegia administration tube being adapted to supply cardioplegia solution to the patient's heart.

The positive displacement pump is adapted for pumping fluid through the cardioplegia administration tube.

The mixing system controls the ratio of cardioplegia medication and blood or blood substitute in the cardioplegia administration tube. The mixing system comprises pinch valves for alternately-continually pinching the cardioplegia and blood supply tubes to close and open the cardioplegia and blood supply tubes such that only one of the cardioplegia and blood supply tubes is open at a time, and a controller for controlling the intervals during which the pinch valves are open with respect to each of the cardioplegia and blood supply tubes to control the ratio of the cardioplegia medication and blood or blood substitute administered through the cardioplegia administration tube.

The pinch valves can comprise a single double-acting solenoid valve that simultaneously allows one of the cardioplegia and blood supply tubes to open as it closes the other of the cardioplegia and blood supply tubes, or the pinch valves can comprise separate solenoid valves for each tube.

The tubing set may also include a recirculation tube, in which case the mixing system might also include a pinch valve for opening and closing the recirculation tube, the controller allowing only one of the cardioplegia supply, blood supply, and recirculation tubes to be open at any give time. A pressure transducer can monitor the pressure in the cardioplegia administration tube, and in response to a pressure exceeding a predetermined threshold, the controller can cause the fluid to open the recirculation tube pinch valve to simply recirculate. Also, the recirculation line provides a recirculation option to the surgeon who might wish to temporarily discontinue the administration of cardioplegia solution.

In a preferred embodiment of the invention, the tubing set can be provided as part of a cassette adapted to interfit with the control unit. The cassette would contain at least the cardioplegia and blood supply tubes, and preferably the recirculation tube as well. The cassette functions to hold these tubes, and position them properly with respect to the controller so that the pinch valves on the controller can operate to open and close the tubes.

The method of this invention provides for the mixing and administering cardioplegia medication and/or blood to a patient's heart during cardiopulmonary bypass surgery. Generally, this method comprises the steps of providing a tubing set, comprising a cardioplegia supply tube in fluid communication with a source of cardioplegia medication, a blood supply tube in fluid communication with a source of blood or blood substitute, and a cardioplegia administration tube connected to the downstream ends of the cardioplegia and blood supply tubes; mounting the cardioplegia administration tube in a positive displacement pump for pumping fluid through the cardioplegia administration tube; mounting the cardioplegia and blood supply tubes in pinch valves; and alternately-continually pinching the cardioplegia and blood supply tubes with the pinch valves to close and open the cardioplegia and blood supply tubes such that only one of the cardioplegia and blood supply tubes is open at a time, controlling the intervals during which the pinch valves are open with respect to each of the cardioplegia and blood supply tubes to control the ratio of the cardioplegia medication and blood or blood substitute administered through the cardioplegia administration tube.

The system and method of the present invention allow the composition of the cardioplegia solution to be easily changed without affecting the flow rate, which is determined by the pump. Moreover, the system and method allow the flow rate of cardioplegia solution to be changed without affecting the composition of the solution, which is determined by the controller. Finally, the system and method provide for the delivery of the cardioplegia solution in a closed, sterile pathway. The tubing set can be made to be quickly attached to and removed from the controller and the pump, so that it can be disposed of after use, eliminating the need to clean or sterilize the controller and pump after each use.

These and other features and advantages of the invention will be in part apparent, and in part pointed out hereinafter.

BRIEF DESCRIPTION OF THE DRAWINGS

FIG. 3 is a schematic diagram of an alternate construction of the first embodiment of a cardioplegia administration system;

FIGS. 4A and 4b are timing diagram, illustrating the control of the alternate construction of the first embodiment;

FIG. 5 is a schematic diagram of a second embodiment of a cardioplegia administration system constructed according to the principles of this invention;

FIGS. 6A, 6b, and 6c are timing diagram, illustrating the control of the system of the second embodiment;

Corresponding reference numerals indicate corresponding parts throughout the several views of the drawings.

DETAILED DESCRIPTION OF THE PREFERRED EMBODIMENT

Figure 1:
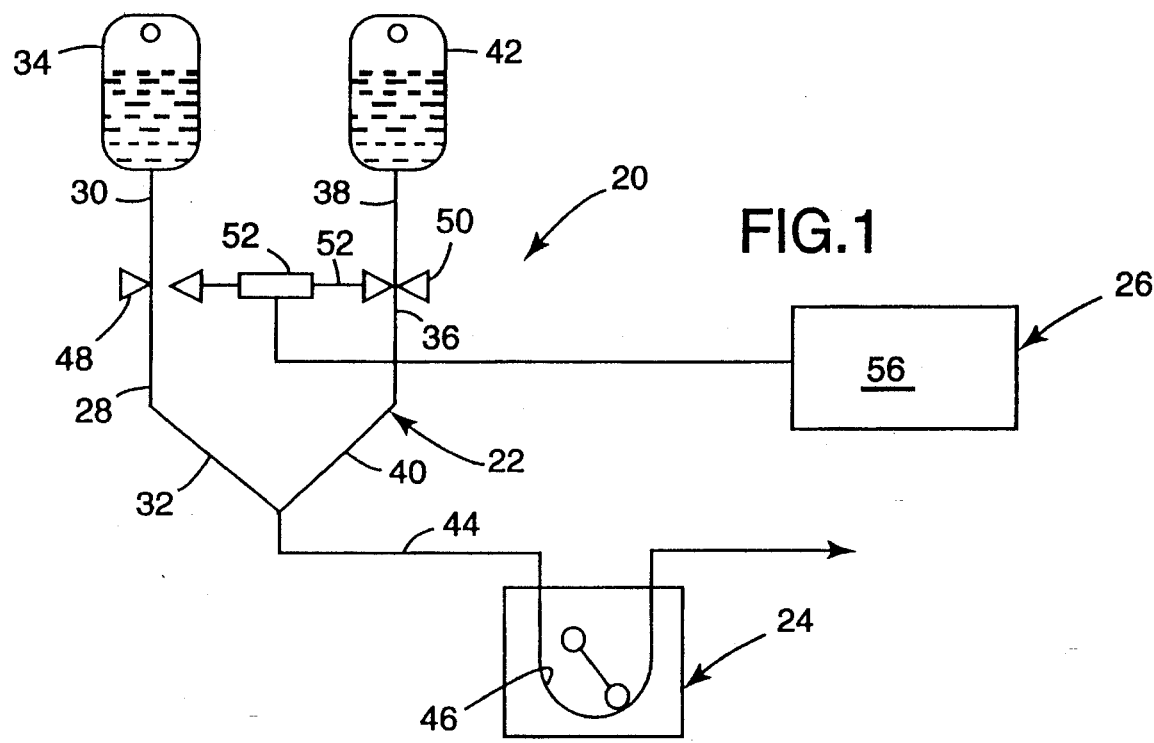
FIG. 1 is a schematic diagram of a first embodiment of a cardioplegia administration system constructed according to the principles of this invention.

A first embodiment of a cardioplegia administration system constructed according to the principles of this invention is shown schematically as 20 in FIG. 1. The system 20 comprises a tubing set 22, a positive displacement pump 24, and a mixing system 26.

The tubing set 22 comprises a cardioplegia supply tube 28, having upstream and downstream ends 30 and 32, respectively. The upstream end 30 of the cardioplegia supply tube 28 is adapted to be connected to a source 34 of cardioplegia medication. The tubing set 22 also comprises a blood supply tube 36, having upstream and downstream ends 38 and 40, respectively. The upstream end 38 of the blood supply tube 36 is adapted to be connected to a source 42 of blood or blood substitute. The tubing set 22 also comprises a cardioplegia administration tube 44 connected to the downstream ends 32 and 40, respectively, of the cardioplegia supply tube 28 and the blood supply tube 36. The cardioplegia administration tube 44 is adapted to supply a cardioplegia solution consisting of cardioplegia medication and/or blood or blood substitute to the patient's heart.

The positive displacement pump 24 is preferably a conventional roller pump, with a track 46 for receiving a portion of the cardioplegia administration tube 44.

The mixing system 26 comprises pinch valves for alternately but continually pinching one of the cardioplegia and blood supply tubes 28 and 36, to open and close these tubes so that only one of these tubes is open at any given time. In system 20, the pinch valves comprise seats 48 and 50 for receiving the cardioplegia and blood supply tubes 28 and 36. The pinch valves also comprise a solenoid 52 positioned so that the plunger 54 of the solenoid impinges on either the cardioplegia supply tube 28 or the blood supply tube 36. The solenoid 52 is preferably positioned so that when the solenoid is not energized, the plunger 54 impinges on the cardioplegia supply tube 28, and when the solenoid is energized (as shown in FIG. 1) the plunger 54 impinges on the blood supply tube 36. The arrangement provides a fail-safe mode in which the system continues to provide blood or blood substitute through the cardioplegia administration tube 44 in the event of failure of the mixing system 26.

Figure 2:
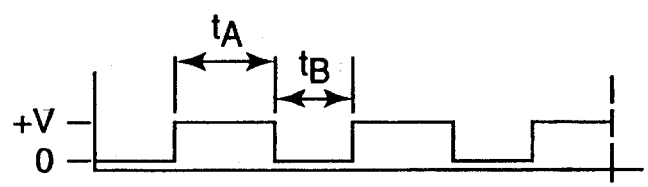
FIG. 2 is a timing diagram, illustrating the control of the first embodiment of the cardioplegia administration system.

The mixing system 26 also comprises a controller 56, that controls the solenoid 52 to control the composition of the fluid supplied to the cardioplegia administration tube 44. As shown on the FIG. 2 timing diagram, when the controller 56 applies no voltage to the solenoid 52, the plunger 54 impinges on the cardioplegia supply tube 38, indicated by $t_B$ on FIG. 2. When the controller 56 applies a positive voltage +V to the solenoid 52, the plunger 54 moves from its position pinching the cardioplegia supply tube 28 to a position pinching the blood supply tube 36 as shown in FIG. 1. This is indicated by $t_A$ on FIG. 2. Because the pump 24 provides a constant flow rate of fluid through the cardioplegia administration tube 44, the controller 56 can control the relative proportions of cardioplegia solution and blood or blood substitute supplied to the cardioplegia administration tube 44, by controlling the amount of time each of the cardioplegia and blood supply tubes 28 and 36 is open. The content of the cardioplegia solution is in direct proportion to the relative amounts of time $t_A$ and $t_B$ each supply tube 28 or 36 is open.

An alternate construction of the first embodiment of the cardioplegia administration is shown as 20' in FIG. 3. The system 20' is similar to system 20, and corresponding parts are identified with corresponding reference numerals. However, instead of a single solenoid 52, the system 20' employs two solenoids 60 and 62. The solenoid 60 has a plunger 64 which, when the solenoid 60 is energized, pinches the cardioplegia supply tube 28. Similarly, solenoid 62 has a plunger 66 which, when the solenoid 62 is energized, pinches the blood supply tube 36. The controller 56 provides signals to the solenoids 60 and 62 to simultaneously energize one of the solenoids while de-energizing the other of the solenoids, so that only one of the cardioplegia and blood supply tubes 28 and 36 is open at any time. As shown in the timing diagram of FIG. 4A and 4b, when the controller 56 provides a positive voltage +V to solenoid 60, it provides 0 voltage to solenoid 62, thus solenoid 60 is energized, solenoid 62 is not energized, and the blood supply tube 36 is open while the cardioplegia supply tube 28 is closed. This is indicated as $t_A$ in FIGS. 4A and 4b. Similarly, when the controller 56 provides a positive voltage +V to solenoid 62, it provides 0 voltage to solenoid 60. This is indicated by $t_B$ in FIGS. 4A and 4b. (Of course, one of the solenoids 60 or 62 could be biased oppositely of the other so that the same signal causes one valve to open and the other to close. This would also allow a selection of one of the supply tubes 28 and 36 to remain open in the event of a power failure. As with system 20, the controller 56 controls the relative proportions of cardioplegia solution and blood or blood substitute applied to the cardioplegia administration tube 44 by controlling the amount of time each of the cardioplegia and blood supply tubes 28 or 36 is open. The tubes 28 and 36 in systems 20' may be of sizes selected so that if there is a failure of the mixing system 26, the pinch valves open and fluid of a preselected composition (determined by the relative sizes of the tubes) is delivered to the cardioplegia administration tube 44.

A second embodiment of a cardioplegia delivery system constructed according to the principles of this invention is indicated generally as 100 in FIG. 5. The system 100 is similar to system 20', described above. The system 100 comprises a tubing set 102, a positive displacement pump 104, and a mixing system 106.

The tubing set 102 comprises a cardioplegia supply tube 108, having upstream and downstream ends 110 and 112, respectively. The upstream end 110 of the cardioplegia supply tube 108 is adapted to be connected to a source 114 of cardioplegia medication. The tubing set 102 also comprises a blood supply tube 116, having upstream and downstream ends 118 and 120, respectively. The upstream end 118 of the blood supply tube 116 is adapted to be connected to a source 122 of blood or blood substitute. The tubing set 102 also comprises a cardioplegia administration tube 124 connected to the downstream ends 112 and 120, respectively, of the cardioplegia supply tube 108 and the blood supply tube 116. The cardioplegia administration tube 124 is adapted to supply cardioplegia solution consisting of cardioplegia medication and/or blood or blood substitute to the patient's heart.

Unlike the tubing set 22 described above, the tubing set 102 also comprises a recirculation tube 126, that parallels a portion of the cardioplegia administration tube 124, for recirculating cardioplegia fluid around the pump 104, as described in more detail below.

The positive displacement pump 104 is preferably a conventional roller pump, with a track 128 for receiving the portion of the cardioplegia tube 124 that is parallel to the recirculation tube 126.

The mixing system 106 comprises pinch valves for alternately but continually pinching two of the cardioplegia supply tube 108, blood supply tubes 116, and the recirculation tube 126, to open and close these tubes so that only one of these tubes is open at any given time. In system 100, the pinch valves comprise seats 130, 132 and 134, for receiving the cardioplegia supply tube 108, the blood supply tube 116 and the recirculation tube 126, respectively. The pinch valves also comprise solenoids 136, 138, and 140. The solenoid 136 has a plunger 142 which, when the solenoid 136 is energized, pinches the cardioplegia supply line 108. Similarly, solenoid 138 has a plunger 144 which, when the solenoid 138 is energized, pinches the blood supply tube 116. Similarly, solenoid 140 has a plunger 146 which, when the solenoid 140 is energized, pinches the recirculation tube 126.

The mixing system also comprises a controller 148, that controls the solenoids 136, 138, and 140 to control the composition of the fluid supplied to the cardioplegia administration tube 124. As shown on the timing diagrams of FIGS. 6A, 6b, and 6c, when the controller 148 applies a positive voltage +V to the solenoid 136, the plunger 142 moves from its position pinching the cardioplegia supply tube 108, opening the tube 108. The controller 148 simultaneously applies a 0 voltage to the solenoids 138 and 140, so that the blood supply tube 116 and the recirculation tube 126 are pinched closed. When the controller 144 applies a positive voltage +V to the solenoid 138, the plunger 144 moves from its position pinching the blood supply tube 116, opening the tube 116. The controller 148 simultaneously applies a 0 voltage to the solenoids 130 and 134, so that the cardioplegia supply tube 108 and the recirculation tube 126 are pinched closed. When the controller 148 applies a positive voltage +V to the solenoid 140, the plunger 146 moves from its position pinching the recirculation tube 126, opening the tube 126. The controller 148 simultaneously applies a 0 voltage to the solenoids 136 and 138, so that the cardioplegia supply tube 108 and the blood supply tube 116 are closed. (As discussed above, with regard to the first embodiment, the solenoids may be oppositely biased from each other so that the same signal causes one solenoid to open and another to close. This arrangement also allows a selection of one of the valves to remain open in the event of a power failure.)

Because the pump 104 provides a constant flow rate, the controller 148 can control the relative proportions of the cardioplegia medication and blood or blood substitute supplied to the cardioplegia delivery tube 124, by controlling the amount of time each of the cardioplegia supply tube 108 ($t_A$ in FIG. 6A, 6b and 6c) and blood supply tube 116 ($t_B$ in FIG. 6A, 6b and 6c) are open. The content of the cardioplegia solution is in direct proportion to the relative amounts of time each of the supply tubes 108 or 116 is open. The controller 148 can also alleviate pressure build-up by closing the cardioplegia and blood supply tubes 108 and 116, and simply recirculating the cardioplegia solution by opening the recirculation tube 126. The system 100 also includes a pressure transducer 150 connected to the controller 148 with a pressure line 151, that monitors the pressure of the cardioplegia solution in the cardioplegia administration tube 124, and provides this information to the controller 148. In response, the controller can energize the solenoid 140, and de-energize solenoids 136 and 138, opening the recirculation tube 126. This is represented by $t_R$ in FIGS. 6A, 6b and 6c. Controls can also be provided to allow the surgeon to select the recirculation mode to temporarily discontinue the administration of cardioplegia solution.

The controller 148 may optionally include a module 152 and position sensors for monitoring the status of the solenoids 136, 138, and 140. These position sensors may be, for example, limit switches 154, 156 and 160 that are opened or closed depending upon the position of solenoids 136, 138 and 140. The data on the positions of the solenoids from the sensors can be provided to the controller 148 via the module 152. The controller 148 can implement a fail safe procedure, or simply shut the system 100 down in the event of an error. For example, the controller 148 could remove power to all of the solenoids if it detects one of the following conditions: (1) More than one pinch valve is open; (2) None of the pinch valves is open; or (3) A valve position is different from the control signal. Alternatively, the solenoids could be configured so that in the event of a failure of the mixing system 106, one or both of the supply tubes 108 and 116 remain open while recirculation tube 126 is closed. In the event both supply tubes 108 and 116 remain open, the composition of the fluid supplied to cardioplegia administration tube 124 is a preselected composition (determined by the relative sizes of supply tubes 108 and 116).

The controller 148 also includes a selection module 162 for setting the composition and the pressure threshold.

Figure 7A:
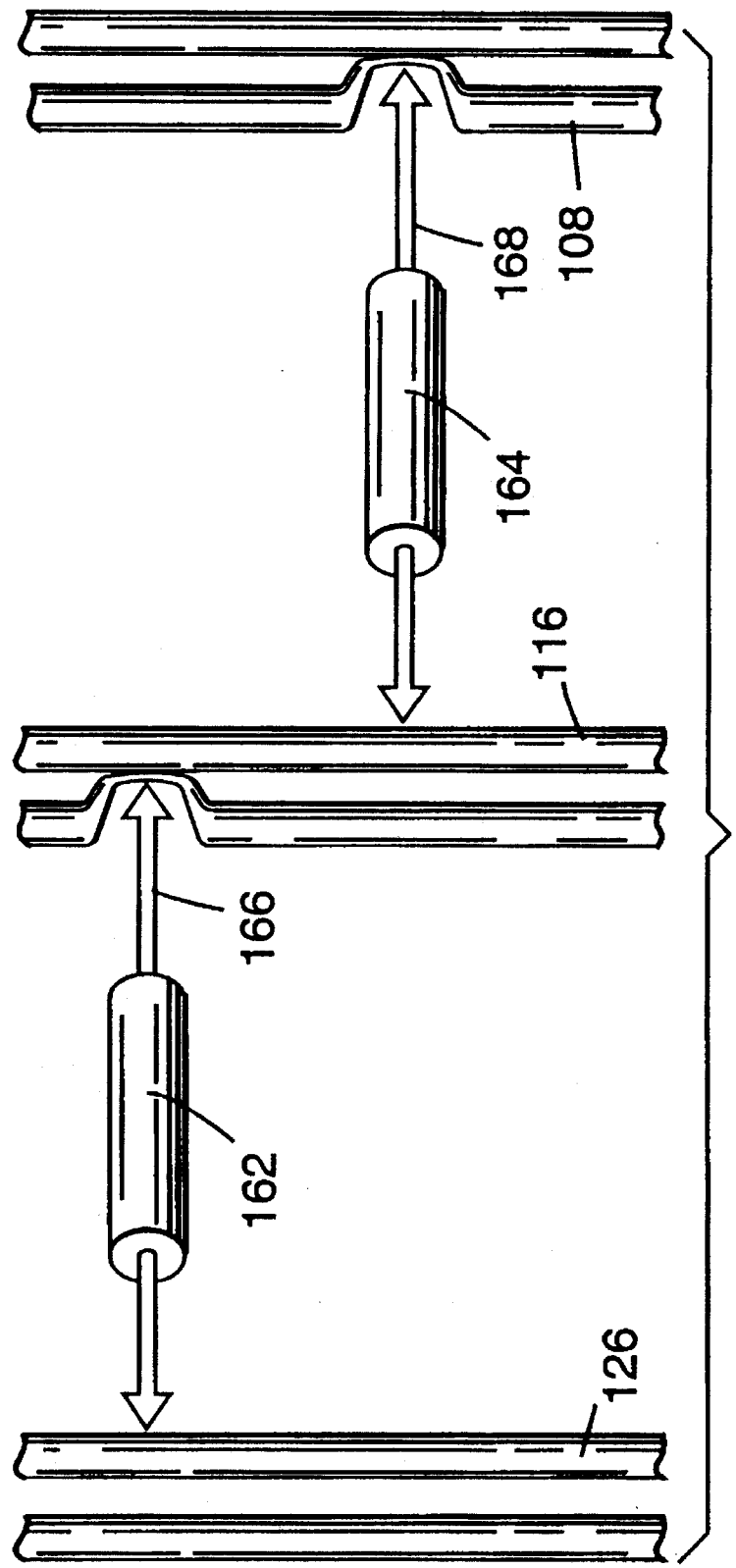
FIG. 7A is a view of an alternate construction of the second embodiment with the recirculation tube open.
Figure 7B:
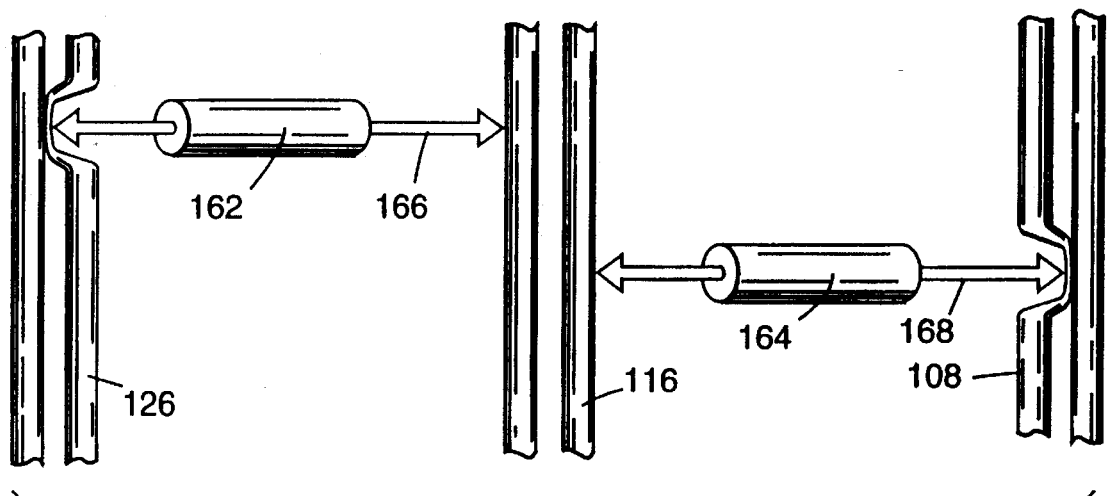
FIG. 7B is a view of an alternate construction of the second embodiment with the blood supply tube open.
Figure 7C:
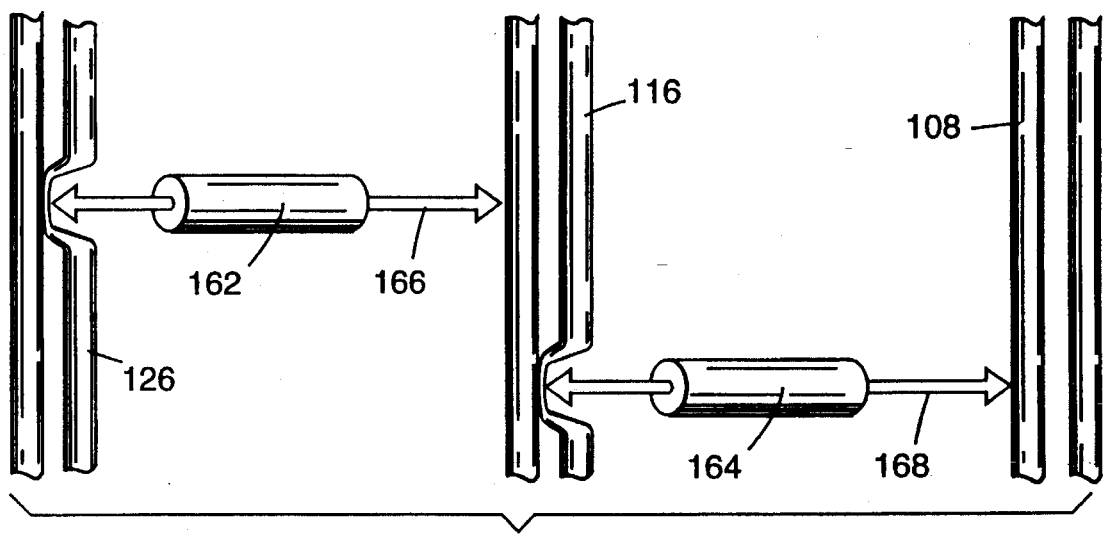
FIG. 7C is a view of an alternate construction of the second embodiment with the cardioplegia supply tube open.

An alternate arrangement of the pinch valves of the second embodiment employing two double-acting solenoids 162 and 164 is illustrated in FIG. 7. As shown in FIG. 7A, solenoids 162 and 164 are de-energized. The plunger 166 of the solenoid 162 impinges on the blood supply tube 116, closing it. The plunger 168 of the solenoid 164 impinges on the cardioplegia supply tube 108, closing it. The recirculation tube 126 is left open. As shown in FIG. 7B, when only the solenoid 162 is energized, the plunger 166 of the solenoid 162 impinges on the recirculation tube 126, closing it. The plunger 168 of the solenoid 164 impinges on the cardioplegia supply tube 108, closing it. The blood supply tube 116 is left open. As shown in FIG. 7C, when both the solenoids 162 and 164 are energized, the plunger 166 of the solenoid 162 impinges on the recirculation tube 126, closing it, and the plunger 168 of the solenoid 164 impinges on the blood supply tube 116. The cardioplegia supply tube 108 is left open. By maintaining the solenoid 162 energized and alternately energizing and de-energizing the solenoid 164, the cardioplegia supply tube 108 and the blood supply tube 116 are alternately opened and closed.

Figure 8:
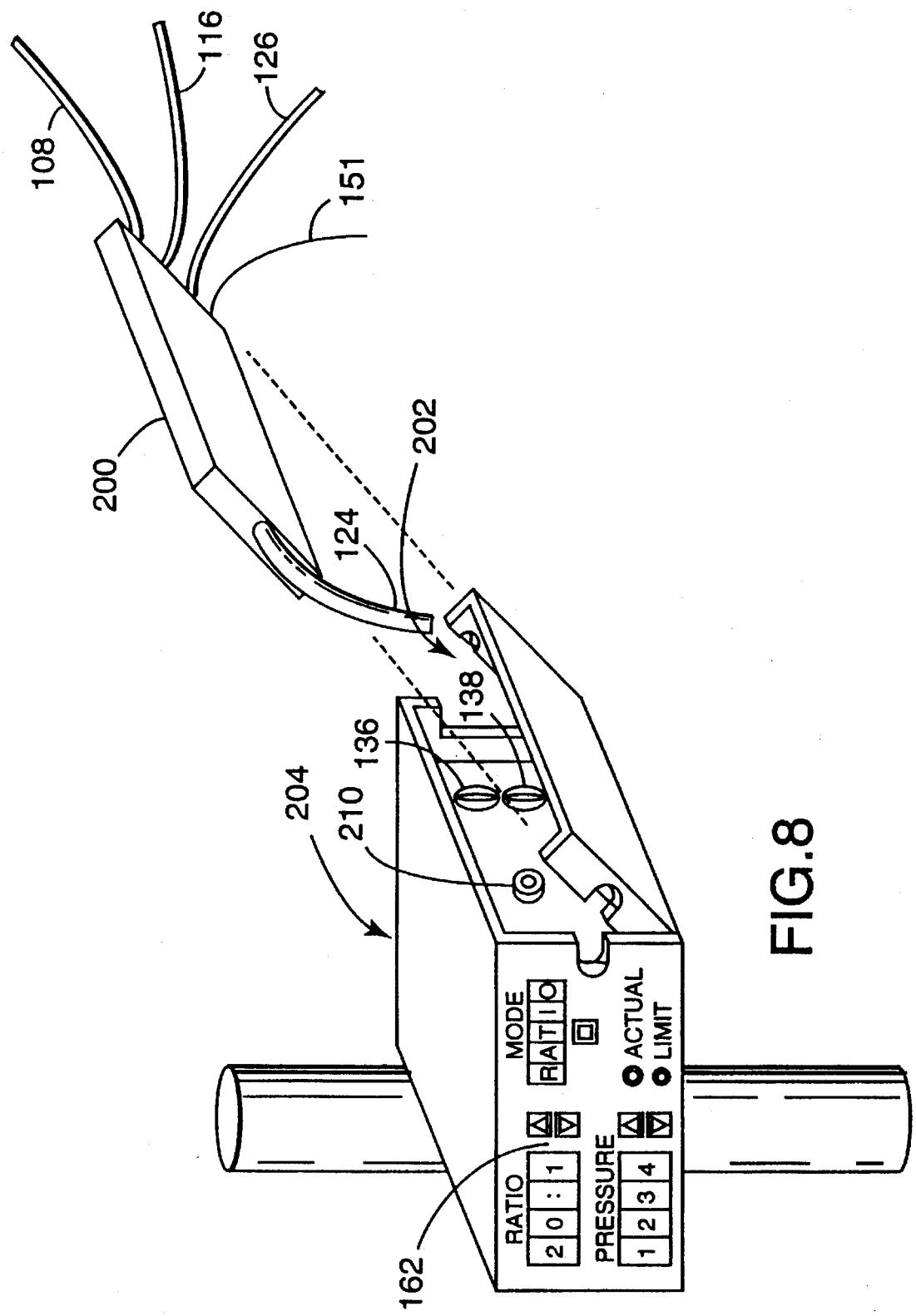
FIG. 8 is a drawing of a disposable cassette system for implementing the system of the second embodiment.
Figure 9:
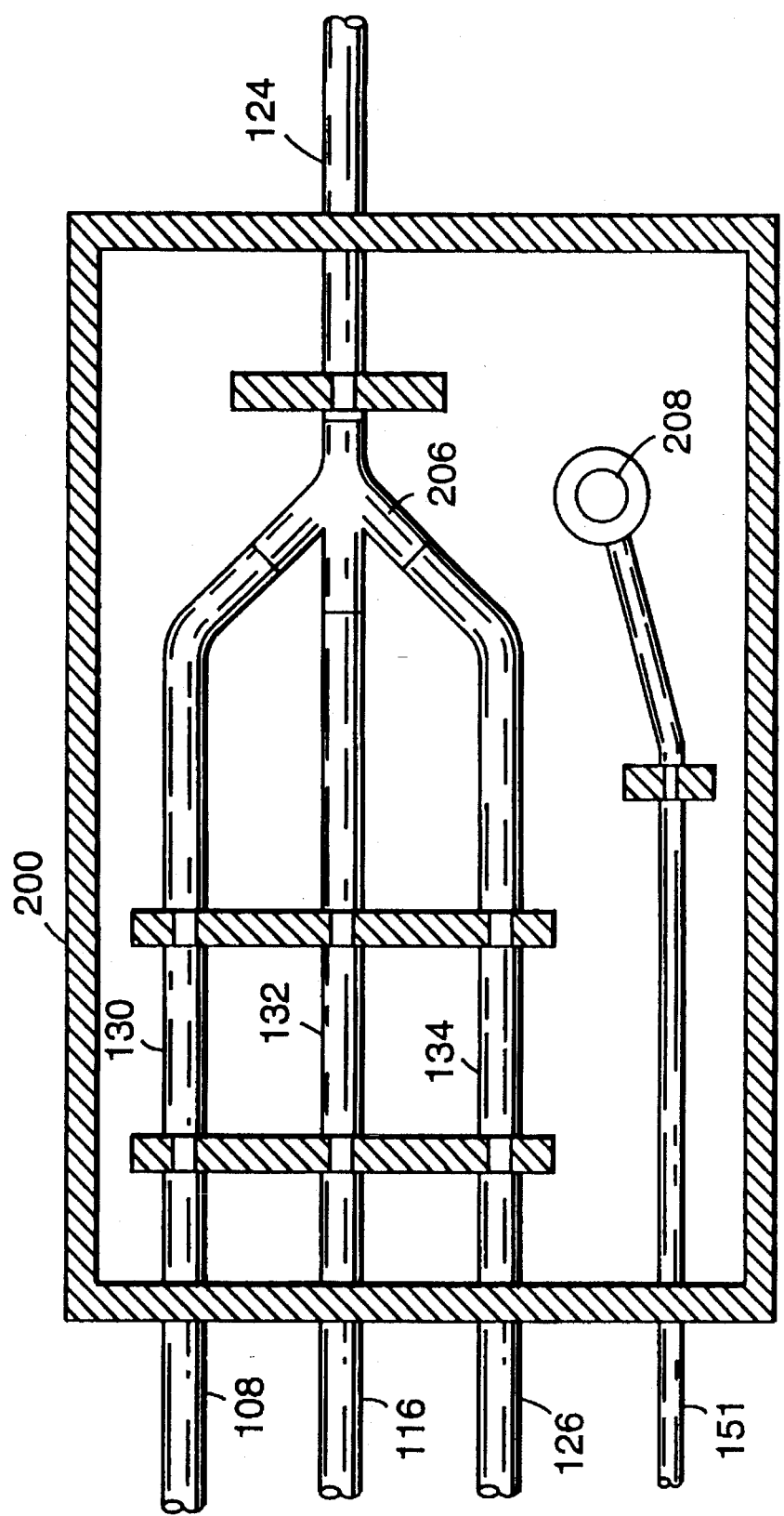
FIG. 9 is a plan view of the cassette for implementing the second embodiment.

As shown in FIG. 8, the tubing set can be incorporated into a cassette 200, adapted to be fit into a socket 202 in the mixing system unit 204. The cassette 200 comprises a box-like frame containing a three-way connector 206 joining the cardioplegia supply tube 108, the blood supply tube 116, and the recirculation tube 126, all to the cardioplegia administration tube 124, as shown in FIG. 9. The cassette 200 may also include a pressure line 151 extending to the pressure transducer 150. In the cassette 200, the pressure line 151 connects to a contact 208 which contacts a contact 210 when the cassette is properly seated in socket 202. The cassette 200 supports the tubes, and may even form part of the seats 130, 132 and 134 of the pinch valves against which the plungers 142, 144 and 146 of the solenoids 136, 138 and 140 act to pinch closed their respective tubes. To this end, the back of the cassette 200 is either open, or has one or more openings allowing access to the separate tubes 108, 116 and 126 by the solenoid plungers on the mixing system unit 204. The cassette also serves to contain the noise from the activation of the plungers so that the system operates quietly.

Figure 10:
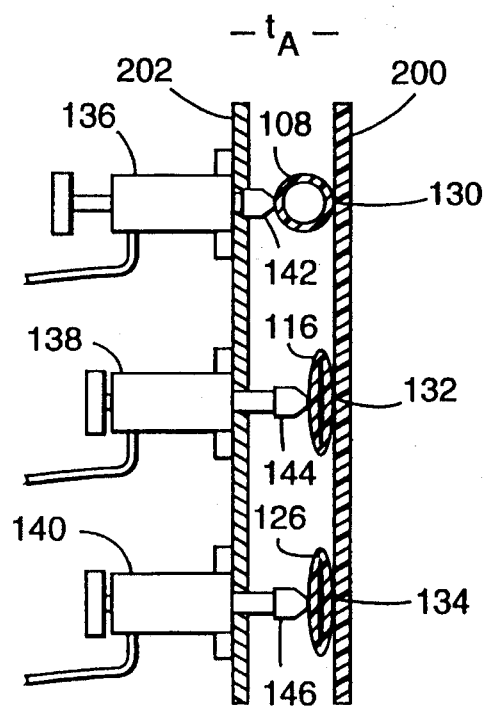
FIG. 10 is a cross-sectional view through the cassette, showing the cardioplegia supply tube open.
Figure 11:
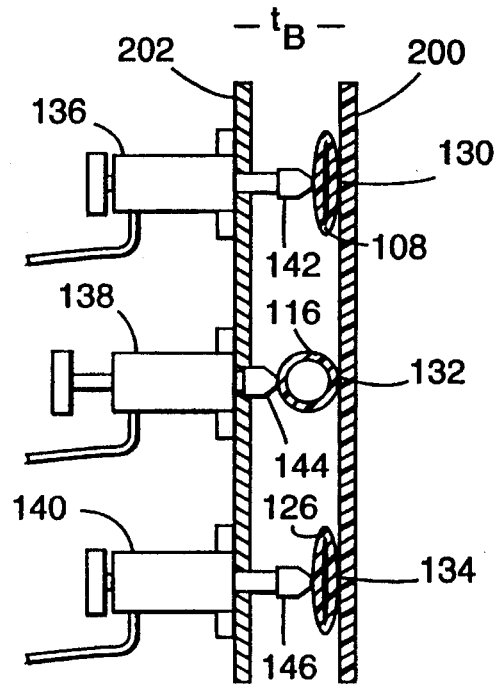
FIG. 11 is a cross-sectional view through the cassette, showing the cardioplegia blood supply tube open.
Figure 12:
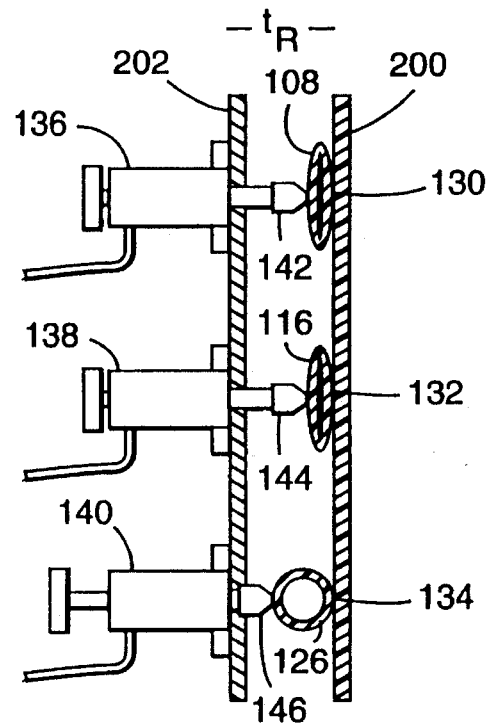
FIG. 12 is a cross-sectional view through the cassette, showing the recirculation tube open.

The mixing system unit 204 is adapted to receive the cassette 200 to position the tubes 108, 116 and 124 so that the solenoids 136, 138, and 140 can pinch the various tubes 108, 116 and 124 closed. As shown in FIG. 10, during the period $t_A$ on the timing diagram of FIGS. 6A, 6b and 6c, the plunger 142 of solenoid 136 on unit 202 is energized to unpinch the tube 108 in seat 130 in cassette 200. The plungers 144 of solenoid 138, and 146 of solenoid 140, on unit 202 are de-energized to pinch the tubes 116 and 124 in their respective seats 132 and 134 in the cassette 200. As shown in FIG. 11, during period $t_B$, the plunger 144 of solenoid 138 on unit 202, is energized to unpinch the tube 116 in seat 132 in cassette 200. The plungers 142 of solenoid 136 and 146 of solenoid 140 on unit 102 are de-energized to pinch the tubes 108 and 124 in their respective seats 130 and 134 in the cassette 200. As shown in FIG. 12, during period $t_R$, the plunger 146 of solenoid 140 on unit 202, is energized to unpinch the recirculation tube 126 in seat 134 in cassette 200. The plungers 142 of solenoid 154 and 144 of solenoid 136 on unit 202 are de-energized to pinch tubes 108 and 16 in their respective seats 130 and 132 in the cassette 200.

OPERATION

The systems 20 and 20' of the first embodiment are quickly and easily set up for the administration of cardioplegia to a patient undergoing cardiac surgery. The tubing set 22 is first connected to the sources of cardioplegia medication and blood or blood substitute. The end 30 of the cardioplegia supply tube 28 is connected to a source 34 of cardioplegia medication, which may be, for example, a flexible bag. The end 38 of the blood supply tube 36 is connected to a source 42 of blood or blood substitute, which may be, for example, a flexible bag. A portion of the tube 28 is then placed in the seat 48 of the pinch valve, and a portion of the tube 36 is placed in the seat 50 of the pinch valve. A portion of the cardioplegia administration tube 44 is then placed in the track 46 of the roller pump 24. The system is primed. The tubing set 22 provides a sterile containment, mixing, and delivery for the cardioplegia solution and blood or blood substitute. The tubing set 22 is designed to minimize the internal volume, and thus the amount of cardioplegia medication and blood or blood substitute used.

The system 20 or 20' is then ready for use. The end of the cardioplegia administration tube 44 is connected to the patient's heart, and the controller 56 is programmed with the desired composition of the cardioplegia solution to be delivered to the patient's heart. In system 20, the controller 56 alternately energizes and de-energizes the solenoid 52 so that the plunger alternately opens cardioplegia supply tube 28 and closes blood supply tube 36 for a period $t_A$, and opens the blood supply tube 36 and closes cardioplegia supply tube 28 for a period $t_B$. In system 20' the controller 56 alternately energizes solenoid 60 while de-energizing solenoid 62, and energizes solenoid 62 while de-energizing solenoid 60 so that the plunger 64 of solenoid 60 opens the cardioplegia supply tube 28 for a period $t_A$ while the plunger 66 of solenoid 62 pinched the blood supply tube 36 closed, and so that the plunger 66 of the solenoid 62 opens the blood supply tube 36 for a period $t_B$ while the plunger 64 of the solenoid 60 pinches the cardioplegia supply tube 28 closed.

The periods $t_A$ and $t_B$ are automatically determined by the controller 56, taking into account the opening and closing properties of the pinch valves, to provide the selected composition of the cardioplegia solution to the cardioplegia administration tube 44. Because the flow rate is constant, the composition of the cardioplegia solution delivered to the cardioplegia administration tube 44 is in direct proportion to the periods $t_A$ and $t_B$.

Of course, a heat exchanger and a debubbler can be incorporated into the systems 20 and 22' to control the temperature of the cardioplegia fluid, and to remove gas bubbles entrained in the fluid.

The system 100 of the second embodiment is quickly and easily set up for the administration of cardioplegia to a patient undergoing cardiac surgery. The cassette 200 containing part of the tubing set 102 is first connected to the sources of cardioplegia medication and blood or blood substitute. The end 110 of the cardioplegia supply tube 108 is connected to a source 114 of cardioplegia medication, which may be, for example, a flexible bag. The end 118 of the blood supply tube 116 is connected to a source 122 of blood or blood substitute, which may be, for example, a flexible bag. The cassette 200 is then inserted into slot 202 on the mixing device 204, which aligns the cardioplegia supply tube 108, the blood supply the 116, and the recirculation tube 126, with the plungers 142, 144, and 146, of solenoids 136, 138, and 140 of the mixing system device 204. The contact 208 on the pressure transducer line in the cassette 200 is also aligned with a pressure transducer contact 210 on the mixing system device 204. A portion of the cardioplegia administration line 124 that parallels the recirculation tube 126 is installed in the track 128 of the roller pump 104. The tubing set 102 in the cassette 200 provides a sterile containment, mixing, and delivery for the cardioplegia solution and blood or blood substitute. The tubing set 102 is designed to minimize the internal volume, and thus the amount of cardioplegia medication and blood or blood substitute used.

The system 100 is then ready for use. The end of the cardioplegia administration tube 124 is connected to the patient's heart, and the controller 148 is programmed via the selection module 162 with the desired composition of the cardioplegia solution to be delivered to the patient's heart. In system 100, the controller 148 alternately energizes solenoid 136 while de-energizing solenoid 138 (see FIG. 10), and energizes solenoid 138 while de-energizing solenoid 136 (see FIG. 11), so that the plunger 142 of solenoid 136 opens the cardioplegia supply tube 108 for a period $t_A$ while the plunger 144 of solenoid 138 pinches the blood supply tube 116 closed, and so that the plunger 144 of the solenoid 138 opens the blood supply tube 116 for a period $t_B$ while the plunger 142 of the solenoid 136 pinches the cardioplegia supply tube 108 closed.

The periods $t_A$ and $t_B$ are automatically determined by the controller 148, taking into account the opening and closing properties of the pinch valves, to provide the selected composition of the cardioplegia solution to the cardioplegia administration tube 124. Because the flow rate is constant, the composition of the cardioplegia solution delivered to the cardioplegia administration tube 124 is in direct proportion to the periods $t_A$ and $t_B$.

The pressure transducer 150 monitors the pressure in the cardioplegia administration tube 124, and if the pressure exceeds a predetermined threshold that may be set with the selection module 162, the controller 148 causes the plungers 142 and 144 of the solenoids 136 and 138 to close, closing the cardioplegia and blood supply tubes 108 and 116. The controller 148 also causes the plunger 146 of solenoid 140 to open the recirculation tube 126, allowing the cardioplegia solution to simply recirculate in a loop through tubes 124 and 126. See FIG. 12. The selection module 162 can also allow the user to enter the recirculation mode on command.

The limit stitches 154, 156, and 158 monitor the states of the solenoids 136, 138, and 140, and provide this information to the controller 148 via the safety module 152. If an error in a solenoid state is detected, the controller can take corrective action, shut down the system 100, or sound an alarm.

Of course, a heat exchanger and a debubbler can be incorporated into the systems 100 to control the temperature of the cardioplegia fluid, and to remove gas bubbles entrained in the fluid. Such heat exchangers (not shown) could be of the types described in U.S. Pat. No. 4,846,177 on Combination Fluid Path and Mount for Heat Exchanger, which is incorporated herein by reference, or in co-pending U.S. patent application Ser. No. 07/951,725; filed Sep. 25, 1992 by William G. O'Neill and Timothy P. Walker, on "Inline Heat Exchanger and Cardioplegia System", which is incorporated herein by reference.

As an alternative to solenoids, stepper motors could be provided to drive the pinch valves.

As various changes could be made in the above constructions and methods without departing from the scope of the invention as defined in the claims, it is intended that all matter contained in the above description or shown in the accompanying drawings shall be interpreted as illustrative and not in a limiting sense.

We claim:

1. A replaceable tubing set cassette adapted for use with a mixer device for selectively mixing two or more medical fluids, the tubing set cassette comprising:

a first supply tube, a second supply tube, and a mixing tube, the first supply tube having upstream and downstream ends, the upstream end of the first supply tube being adapted to connect the first supply tube to a source of a first biological or medical fluid; the second supply tube having upstream and downstream ends, the upstream end of the second supply tube being adapted to connect the second supply tube to a source of a second biological or medical fluid; and the mixing tube having an upstream end connected to the downstream ends of the first and second supply tubes, and a downstream end for supplying a mixed fluid comprising a preselected composition of the first and second fluids, the mixing tube having a lumen, in which the first and second fluids are mixed, and an exterior surface separated from the lumen by a tube wall; at least portions of the first and second supply tubes being contained in a cassette that is adapted to be mounted on the mixer device, the cassette having at least one opening therein allowing access to the first and second supply tubes so that the mixer device can selectively pinch the first and second supply tubes closed.

2. The replaceable tubing set cassette according to claim 1 further comprising a recirculation tube having upstream and downstream ends in fluid communication with the mixing tube, a portion of the recirculation tube being in the cassette, and wherein the cassette has an opening therein allowing access to the recirculation tube so that the mixer can selectively pinch the recirculation tube closed.

3. The replaceable tubing set cassette according to claim 2 wherein the cassette comprises a box-like frame.

4. The replaceable tubing set cassette according to claim 3 further comprising a pressure line connected to a contact mounted in the cassette, the contact being adapted for operative engagement with a contact in the device.

5. The replaceable tubing set cassette according to claim 4 further comprising a three-way Y-type connector within the cassette connecting the first supply tube, second supply tube, mixing tube and recirculation tube.

6. The replaceable tubing set cassette according to claim 5 wherein the first supply tube, second supply tube and recirculation tube each include exposed portions within the cassette exposed through the opening to allow access to the exposed portions to allow the mixer device to pinch the exposed portions, the cassette further comprises mounting blocks in the cassette for holding the exposed portions of the first supply tube, second supply tube and recirculation tube across the opening of the cassette.

7. The replaceable tubing set cassette according to claim 6 wherein the mounting blocks hold the exposed portions of the first supply tube, second supply tube and recirculation tube generally parallel to one another.

8. The replaceable tubing set cassette according to claim 2 further comprising a three-way Y-type connector within the cassette connecting the first supply tube, second supply tube, mixing tube and recirculation tube.

9. The replaceable tubing set cassette according to claim 2 wherein the first supply tube, second supply tube and recirculation tube each include exposed portions within the cassette exposed through the opening to allow access to the exposed portions to allow the mixer device to pinch the exposed portions, the cassette further comprises mounting blocks in the cassette for holding the exposed portions of the first supply tube, second supply tube and recirculation tube across the opening of the cassette.

10. The replaceable tubing set cassette according to claim 9 wherein the mounting blocks hold the exposed portions of the first supply tube, second supply tube and recirculation tube generally parallel to one another.

11. The replaceable tubing set cassette according to claim 10 further comprising a three-way Y-type connector within the cassette connecting the first supply tube, second supply tube, mixing tube and recirculation tube.

12. The replaceable tubing set cassette according to claim 1 wherein the cassette comprises a box-like frame.

13. The replaceable tubing set cassette according to claim 1 further comprising a pressure line connected to a contact mounted in the cassette, the contact being adapted for operative engagement with a contact in the device.

14. The replaceable tubing set cassette according to claim 1 further comprising a Y-type connector within the cassette connecting the first supply tube, second supply tube and mixing tube.

15. The replaceable tubing set cassette according to claim

1 wherein the first supply tube and second supply tube each include exposed portions within the cassette exposed through the opening to allow access to the exposed portions to allow the mixer device to pinch the exposed portions, the cassette further comprises mounting blocks in the cassette for holding the exposed portions of the first supply tube and second supply tube across the opening of the cassette.

16. The replaceable tubing set cassette according to claim 15 wherein the mounting blocks hold the exposed portions of the first supply tube and second supply tube generally parallel to one another.

17. The replaceable tubing set cassette according to claim 16 further comprising a Y-type connector within the cassette connecting the first supply tube, second supply tube and mixing tube.

18. The replaceable tubing set cassette according to claim 15 further comprising a pressure line connected to a contact mounted in the cassette, the contact being adapted for operative engagement with a contact in the device.

* * * * *

UNITED STATES PATENT AND TRADEMARK OFFICE
CERTIFICATE OF CORRECTION

PATENT NO. : 5,464,388
DATED : November 7, 1995
INVENTOR(S) : Kenneth E. Merte and William G. O'Neill It is certified that error appears in the above-indentified patent and that said Letters Patent is hereby corrected as shown below:

Col. 1, line 37, "adopted" should read --adapted--.
Col. 1, line 39, "adopted" should read --adapted--.
Col. 2, line 2, "give" should read --given--.
Col. 3, line 1, "diagram," should read --diagrams,--.
Col. 3, line 6, "diagram," should read --diagrams,--.
Col. 4, line 41, "diagram" should read --diagrams--.
Col. 4, line 53, after "failure." insert --)--.
Col. 5, line 31, "tubes" should read --tube--.
Col. 7, line 29, "diagram" should read --diagrams--.
Col. 8, line 41, the second occurrence of "the" should read --tube--.

In Figure 1 there are two number 52's. The first 52 referring to the solenoid is correct, the second "52" referring to the plunger should read --54--.

Signed and Sealed this

Twenty-ninth Day of April, 1997

Attest:

BRUCE LEHMAN

Attesting Officer

Commissioner of Patents and Trademarks